(12) United States Patent
Winter

(10) Patent No.: US 9,050,088 B2
(45) Date of Patent: Jun. 9, 2015

(54) ANASTOMOSIS RING AND ANASTOMOSIS RING ARRANGEMENT

(75) Inventor: Hanno Winter, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 682 days.

(21) Appl. No.: 13/382,221

(22) PCT Filed: Jul. 15, 2010

(86) PCT No.: PCT/EP2010/060155
§ 371 (c)(1),
(2), (4) Date: Jan. 4, 2012

(87) PCT Pub. No.: WO2011/006937
PCT Pub. Date: Jan. 20, 2011

(65) Prior Publication Data
US 2012/0101500 A1 Apr. 26, 2012

Related U.S. Application Data

(60) Provisional application No. 61/225,988, filed on Jul. 16, 2009.

(30) Foreign Application Priority Data

Jul. 17, 2009 (DE) .......................... 10 2009 027 813

(51) Int. Cl.
*A61B 18/14* (2006.01)
*A61B 17/11* (2006.01)
*A61B 17/00* (2006.01)

(52) U.S. Cl.
CPC ............. *A61B 17/11* (2013.01); *A61B 17/1114* (2013.01); *A61B 2017/00504* (2013.01); *A61B 2017/1132* (2013.01)

(58) Field of Classification Search
CPC .. A61B 17/11; A61B 17/1114; A61B 17/115; A61B 17/1155; A61F 2002/044; A61F 2220/0008; A61F 2250/0069; A61F 5/0086
USPC ...................... 606/49–50, 139, 148, 151–154
See application file for complete search history.

(56) References Cited

U.S. PATENT DOCUMENTS 5,346,501 A * 9/1994 Regula et al. ................. 606/151
2005/0055022 A1* 3/2005 Schubert ......................... 606/49
(Continued)

FOREIGN PATENT DOCUMENTS

| CN | 2889184 Y | 4/2007 |
| WO | WO 99/40857 A1 | 8/1999 |
| WO | WO 02/069813 A2 | 9/2002 |
| WO | WO 2005/096954 A2 | 10/2005 |
| WO | WO 2008/125259 A2 | 10/2008 |

OTHER PUBLICATIONS

Harder et al.; "Sequential Single Row Intestinal Anastomosis;" *Chirurg*; 1987; pp. 269-273; vol. 58.
(Continued)

*Primary Examiner* — Rex R Holmes
(74) *Attorney, Agent, or Firm* — Oliff PLC

(57) ABSTRACT

The invention relates to an anastomosis ring and to an anastomosis ring assembly for connecting hollow organs made from human or animal tissue. The anastomosis ring includes a first support ring and a second support ring, which can be coupled with the first support ring for fixating the tissue, so that the support rings are essentially disposed fixated relative to one another. The anastomosis ring is at least partially made form a biofragmentable material which disintegrates after a predetermined time period in a human or animal body. In order to facilitate better tissue connection the anastomosis ring includes at least one energy delivery element connectable with an energy source. The energy delivery element is configured to fuse the tissue at least partially through delivering energy during operations.

14 Claims, 8 Drawing Sheets

(56) References Cited

U.S. PATENT DOCUMENTS

2007/0239260 A1  10/2007  Palanker et al.
2008/0015617 A1   1/2008  Harari et al.
2008/0195091 A1   8/2008  Takashino et al.
2008/0300618 A1  12/2008  Gertner

OTHER PUBLICATIONS

Kawahara et al.; "First Experimental Sutureless End-to-End Laser Anastomosis of the Large Bowel. Short Term Results;" *Dis Colon Rectum*; 1992; pp. 792-798; vol. 35, No. 8.

Kuramoto et al.; "Experimental Laser Anastomosis of the Colon. Long-Term Results and Histologic Findings After Laser Closure of Colotomies;" *Dis Colon Rectum*; 1994; pp. 1198-1204;vol. 37, No. 12.

Cilesiz et al.; "Controlled Temperature Tissue Fusion: Argon Laser Welding of Rat Intestine In Vivo, Part One;" *Lasers in Surgery and Medicine*; 1997; pp. 269-277; vol. 21.

International Search Report dated Oct. 22, 2010 in International Application No. PCT/EP2010/060155.

Written Opinion of the International Searching Authority; Oct. 22, 2010 in International Application No. PCT/EP2010/060155.

\* cited by examiner

A - A

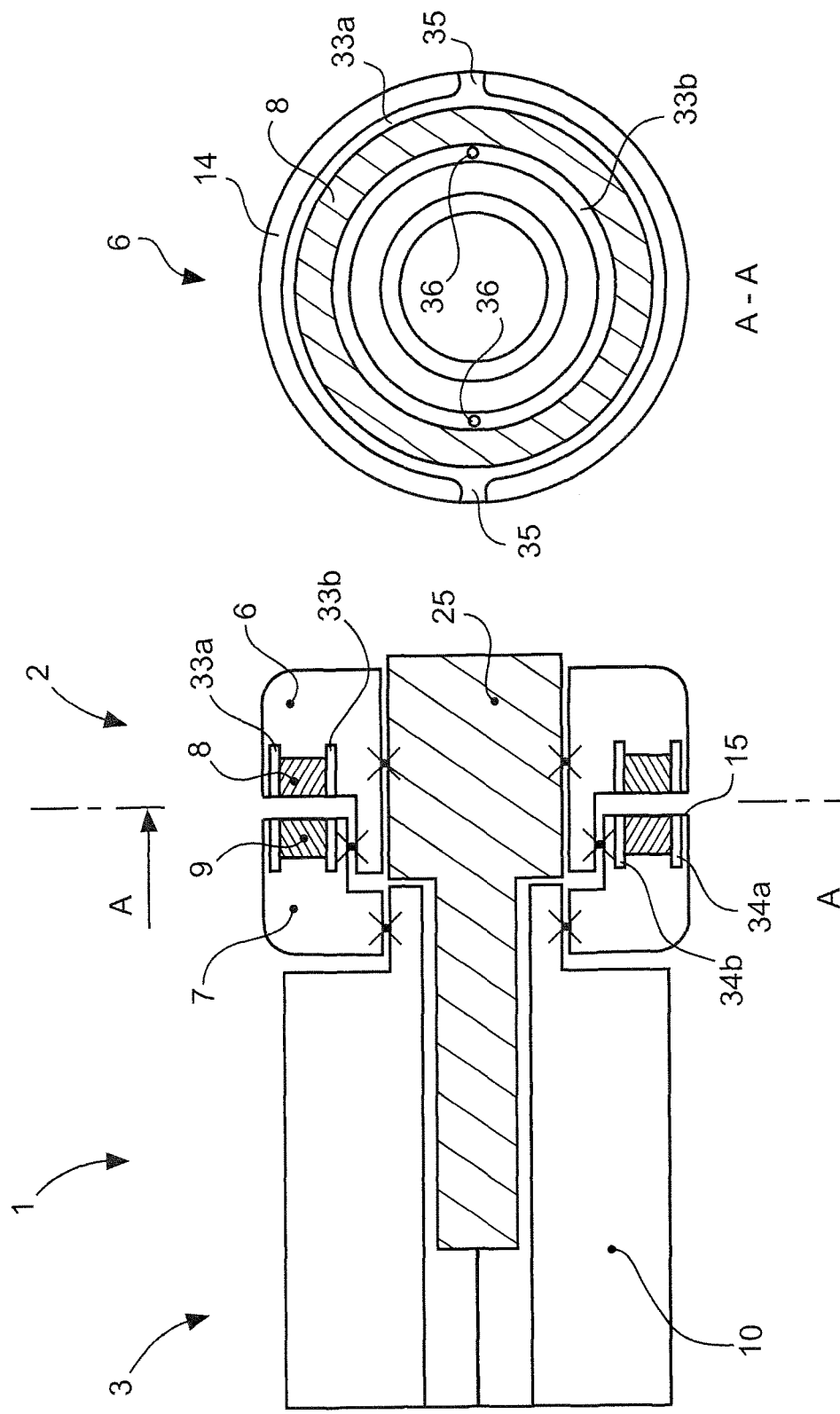

ANASTOMOSIS RING AND ANASTOMOSIS RING ARRANGEMENT

The invention relates to an anastomosis ring for connecting hollow organs of human or animal tissue with a first support ring and a second support ring, which is configured to be coupled with the first support ring for fixating the tissue, so that the support rings are essentially fixated relative to one another.

Furthermore the invention also relates to an anastomosis ring assembly for connecting organs of human or animal tissue.

Joining techniques support wound healing of human or animal tissue, but they do not replace it. Optimum wound closure is characterized by a sufficient blood supply for the tissue edges, by the smallest amount of foreign material that is as biocompatible as possible and by a simple and quick application of the joining technique. Additional factors are undisturbed wound healing and sufficient tightness or strength. With this respect reference is made e.g. to Harder F., Krull C., "sequential single row intestinal anastomosis" Chirurg 58: 269-273 (1987).

Surgeons can rely on a plurality of techniques for wound closure today. A standard for conventional wound closure is still the classic sewing technique. Along with the development of minimally invasive surgical techniques, however, the requirements for a simple and quick application of wound closure techniques have become more stringent. Due to the restricted view of the area where the surgery is performed (2D—depiction, display window), the limited range of motion of the instruments (invariant point at trokars), through a lack of haptic feedback and instruments which are not shaped ergonomically, the manual laproscopic fabrication of a suture or of a knot is very time consuming, straining and in some cases even impossible.

Through the development of clamping suture instruments, the so called staplers, the requirements with respect to a joining technique which can be applied in a simple and quick manner, could be fulfilled to a large extent. This was eventually facilitated by a wide use and improvement of minimally invasive surgery. The stapler technique, however, also had disadvantages, thus e.g. the foreign materials like e.g. titanium clamps which remained in the body of the patient and which are non resorbable increased. Furthermore, the blood supply of the edges of a wound which is important for wound healing deteriorated through staple compression.

Through the development of new techniques like e.g. bipolar high frequency techniques, cost effective and surgically established methods for thermal tissue treatment are available today. Depending on temperature, time and pressure it is possible in principle to fuse (weld) tissue types like e.g. intestinal wall, urethra or skin in order to close wounds. For this purpose, a thermally induced transformation process, denaturization of the proteins provided in human tissue can be used. The electrosurgical fusion of body tissue is described e.g. in US 2007/0239260, WO99/40857 or WO 2008/125259.

Electro surgical tissue fusion is used e.g. for wound closure instead of conventional sutures. Optimum wound closure is a crucial requirement for complication free recovery of a surgically treated patient. Studies confirm that all prior post operative complications after a minimally invasive procedure result from compromised wound healing.

The feasibility of thermo fusion in principle, e.g. of intestinal tissue is known. When assessing wound healing and strength of connection of an intestinal anastomosis after a thermal fusion of the tissue was performed there are however significantly lower strength parameters or burst pressures of thermally fused tissues compared to a stapler suture. Reference is made furthermore to KURAMOTO, S.; RYAN, P. J.; KAWAHARA, M.; MASAKI, Y. (1994): <<Experimental laser anastomosis of colon. Long-term results and histologic findings after laser closure of colotomies>>, Dis Colon Rectum, 37, 1994; KAWAHARA, M.; KURAMOTO, S.; RYAN, P.; STILLWELL, R. (1992): <<First experimental suture less end-to-end anastomosis of the large bowel. Short-term results>>, Dis Colon Rectum, 35, 1992; CILESIZ, I.; THOMSEN, S.; WELCH, A. J. (1997): <<Controlled temperature tissue fusion: argon laser welding of rat intestine in vivo. Part one>>, Lasers Surg Med, 21, 1997.

Besides the suture-, stapler- and thermal fusion technique, there is another alternative method for creating an intestinal anastomosis. Through a so called compression- or anastomosis ring it is possible to clamp two open intestinal ends together through a compression mechanism. This compression ring is made of a biofragmentable material, so that it disintegrates after a couple of weeks in the intestine and so that it is excreted in a natural manner. The compression of the wound edges of the intestine for this amount of time is sufficient, so that the natural wound healing has progressed enough, so that the joint is self supporting after the compression ring has been resorbed. A compression ring and a compression ring applicator are described e.g. in US2008/0015617 A1.

It is the object of the invention to improve the known techniques for creating a tissue connection.

The object is accomplished through the present invention by an anastomosis ring that includes at least one energy delivery element which is connectable with an energy source, wherein the energy delivery element is configured to fuse the tissue by delivering energy at least in sections during operation.

The solution according to the invention has the advantage that a stabile tissue connection is provided, because the tissue is both, fused and fixated through the support rings during the fusion or thereafter. The tissue fusion through the imparted energy supports the natural wound healing, which occurs subsequently during the fixation through the support ring. Thus, it is possible to provide e.g. a thermal fusion of intestinal ends which is fixated through the support rings in the first phase of wound healing and thus facilitates a sufficiently high tightness and strength of the connection.

Joining tissue is a basic activity during almost all surgical procedures, wherein the clinical meaning of an improved wound closure technique is generally high. The complete omission of foreign material remaining in the patient helps to reduce immune defense and possible allergic tissue reactions and supports a natural wound healing without complications. The probability of post operative complications can thus be reduced. It has furthermore become evident that the intended thermal damaging of the tissue which is caused by the fusion improves circulation and thus also natural wound healing.

The anastomosis ring according to the invention facilitates fixating the tissue during the fusion exclusively through the energy delivery elements or through the support rings or through both. After thermal fusion the tissue is then supported through the support rings.

The solution according to the invention can be used e.g. for anastomosis of intestines e.g. after sigma resection or after hemicolectomy. Furthermore an application is possible in urology after a total prostatectomy for urethra—bladder anastomosis.

The invention can be implemented in advantageous embodiments which are described infra.

Thus, the anastomosis ring (2) can be made at least partially from a biofragmentable and/or bioresorbable material which disintegrates after a predetermined period of time in a body of a human or of an animal. Since the anastomosis ring according to the invention in this embodiment is at least partially made from biofragmentable material, it automatically disintegrates after a predetermined time period. Portions of the anastomosis ring which are not biofragmentable and therefore do not disintegrate are configured, so that they can be excreted in a natural manner. Certainly also the entire anastomosis ring can be made from biofragmentable material.

Thus, the first support ring can have a first support surface and the second support ring can have a second support surface, wherein the support surfaces support the tissue during fusion and the energy delivery element is disposed, so that it forms one of the support surfaces, at least in sections. This has the advantage that a direct transfer of fusion energy into the tissue is facilitated.

In a preferred embodiment, an anastomosis ring can include two energy delivery elements, each respectively associated with one of the two support rings, which energy delivery elements are configured as HF electrodes and connectable with an energy source. This has the advantage that already established and reliable high frequency technology can be used. Certainly, the at least one energy delivery element can be configured alternatively or additionally also to deliver other known forms of energy, which are suitable for fusion. Thus, e.g. laser energy, thermal energy generated by a heater element, ultrasound energy or microwave energy can be used for generating tissue fusion. A heating element like e.g. a heating resistor can also be used in combination with HF electrodes.

In order to reduce the thermal dissipation and/or the water content in a tissue during tissue fusion, at least one drainage channel can be configured in at least one of the support surfaces wherein the fluid generated in the tissue during fusion can be drained through the drainage channel.

It has become apparent through testing that a positive pressure can be generated during tissue fusion of hollow organs through electrodes with an annular configuration within an electrode assembly which is closed towards the outside. The positive pressure is created by water vapor created during fusion, wherein the water vapor escapes from the tissue and flows into the closed inner ring of the fusion assembly. When the pressure becomes too high, the water vapor escapes for pressure relief along the fusion seam and can damage or destroy the tissue fusion. In order to prevent such a pressure rise in the anastomosis ring according to the invention, the anastomosis ring can include at least one pressure relief channel, through which a fluid pressure which is created during fusion in the anastomosis ring and which is different from the ambient pressure can be relieved.

The at least one pressure compensation channel constitutes a separate and distinct invention, which can also be used by any other tissue fusion device besides an anastomosis ring in order to yield the advantages recited supra.

In an advantageous embodiment of the present invention the anastomosis ring can include at least one temperature sensor, through which the temperature of the tissue can be detected. The measured temperature can be used for controlling the energy source like e.g. a HF generator in order to thus prevent a strong heating a damaging of the tissue during fusion.

As an alternative or additional means for preventing strong heating or damaging of the tissue, the anastomosis ring can include at least one channel for cooling liquid extending at least in the portion of the energy delivery element, wherein a liquid coolant can be run through the coolant liquid channel. Thus, coolant can be fed through conduits through the support rings through a flow connection, e.g. at an applicator which will be described infra. Thus, the electrically conductive portions of the instrument can be cooled through a water coolant cycle, while fusion energy is applied to the tissue. This limits a tendency of tissue to stick to the electrodes and also limits a thermal effect on a small tissue portion. For example Saline solution (NaCl) can be used as a coolant. The coolant channel can extend directly through the energy delivery elements or proximal to the energy delivery elements.

In order to maintain a natural intestinal activity when the anastomosis ring according to the invention still remains in a body after tissue fusion, the anastomosis ring can include an opening extending at least in axial direction, whose inner width facilitates a natural passage of intestinal contents. Thus, openings can be configured respectively in both support rings, wherein the openings are essentially flush in a coupled condition.

The anastomosis ring according to the invention can certainly be adapted to the size of the hollow organ through its size, diameter and shape. Anastomosis rings according to the invention can be offered in various sizes e.g. with diameters of 25, 28, 31 or 33 mm.

In order to achieve the object recited supra, the anastomosis ring according to the invention includes at least one anastomosis ring according to one of the recited embodiments, at least one applicator disengageably connected with the anastomosis ring for arranging an anastomosis ring within a body, and at least one energy input, whose first end is operatively connected with the energy delivery element and whose second end is connectable with the energy source. Through the applicator the anastomosis ring can be easily inserted into the body of a patient, e.g. into an intestine during an intestinal asastomosis. Thus the distal end of the applicator is disposed within the body of a human or an animal and the proximal end is disposed on the outside thereof. A handle with actuation elements like e.g. a manual switch or lever for activating the fusion energy can be disposed at the proximal end.

In another embodiment the energy input can be at least partially connected to the applicator and/or extend within the applicator. Thus fusion energy is conducted in a very simple manner from an energy source outside the body to the energy delivery element within the body.

It has become apparent that fusion and also natural wound healing can be improved when the tissue layers to be connected with one another are pressed against one another with a certain pressure. Therefore, the anastomosis ring assembly can include at least one fusion force unit which imparts a predetermined fusion force at least during fusing, wherein the fusion force presses the tissue portions which are to be connected against one another. The fusion force unit can be part of the anastomosis ring or part of the applicator. In order to be able to adjust the fusion force in an optimum manner, the fusion force unit can include an adjustment unit through which the fusion force unit is adjustable.

Tests have shown that a particularly good fusion of tissue components can be achieved when the fusion force is varied during fusion. Therefore the fusion force unit can be configured in another advantageous embodiment, so that it imparts at least two different support forces during fusing.

The fusion force can be applied e.g. manually through a handle of the applicator by the surgeon or it can also be applied in a controlled manner by a control unit through a drive.

The invention furthermore relates to a kit for an anastomosis ring assembly for connecting hollow organs made from human or animal tissue including at least one anastomosis ring according to one of the embodiments recited supra, and at least one applicator connectable with the anastomosis ring for arranging the anastomosis ring within a body.

The invention furthermore relates to a method for intestinal anastomosis of two intestinal pieces comprising the following steps:

Inserting an anastomosis ring assembly into an intestine, wherein a first support ring is inserted into a first intestinal piece and a second support ring is inserted into a second intestinal piece, wherein the support rings are portions of an anastomosis ring of the anastomosis ring assembly;

Forcing the support rings together, so that the intestinal pieces contact one another;

Fusing the intestinal pieces through passing high frequency AC current through the intestinal pieces;

Decoupling an applicator of the anastomosis ring assembly from the anastomosis ring and removing the applicator from the intestine;

Supporting the fused intestinal pieces through the remaining anastomosis ring for a predetermined period of time; and Allowing self acting disengagement of the anastomosis ring from the intestinal pieces after a predetermined period of time and excretion of the anastomosis ring.

The invention has the advantage that intestinal pieces are reliably connected with one another.

The invention is subsequently described with reference to advantageous embodiments illustrated in drawing figures. Thus, the various features can be combined in any manner.

Figure 3:
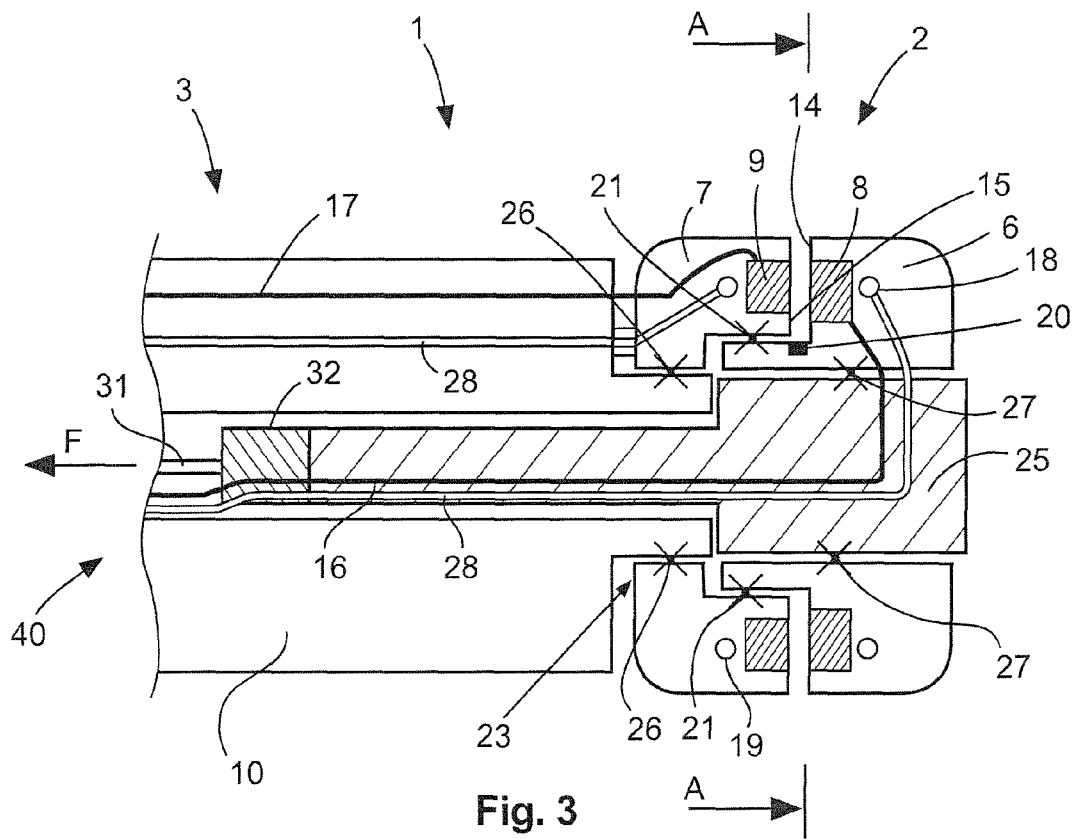
FIG. 3 illustrates a schematic sectional view of the distal end of the anastomosis ring assembly according to the invention with an anastomosis ring according to FIG. 1.
Figure 6:
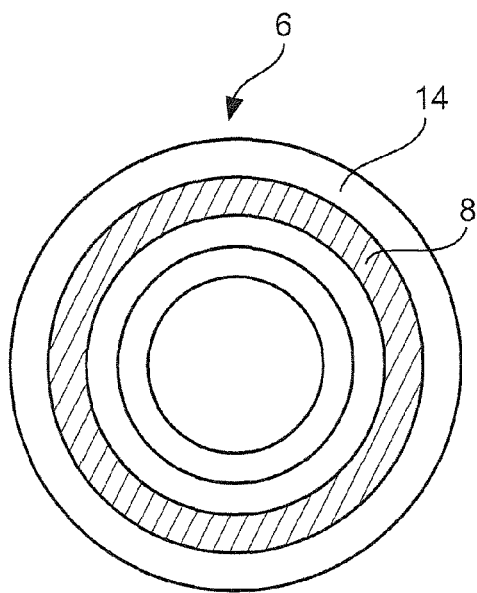
Figure 4A:
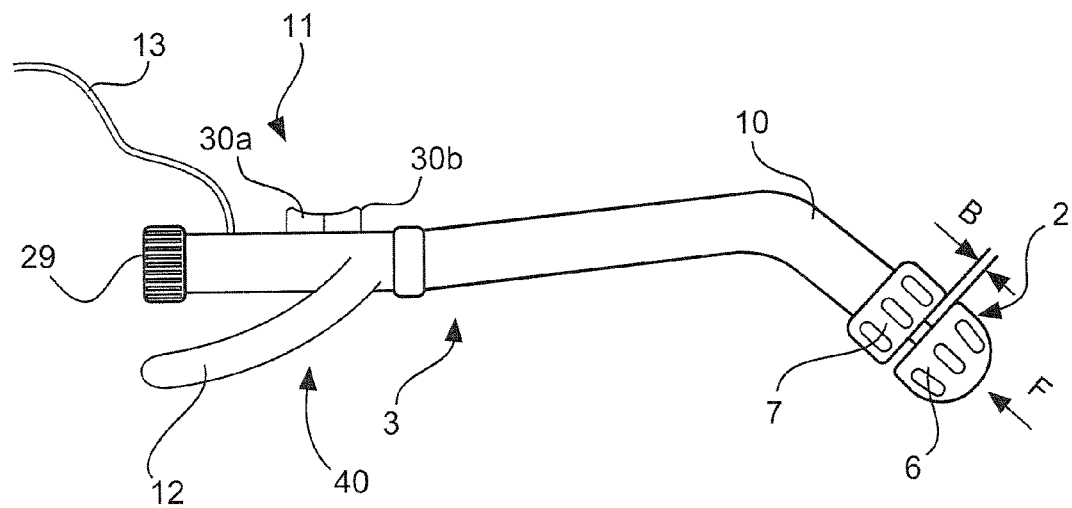
Figure 4B:
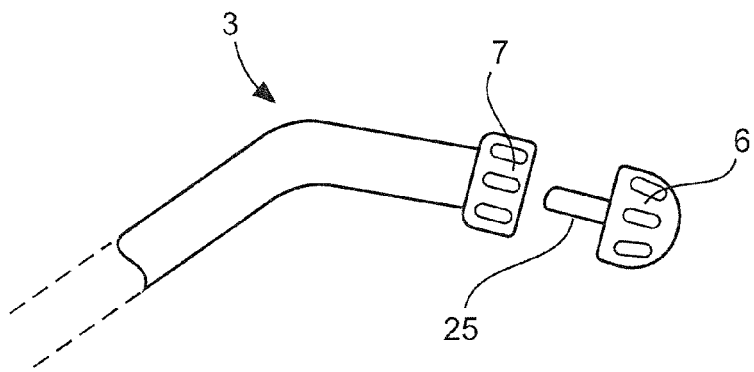
Figure 4C:
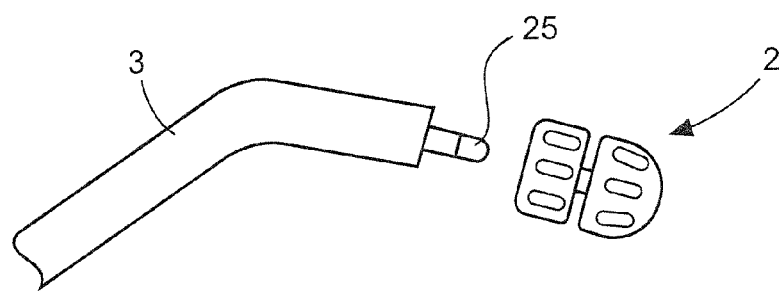
Figure 10:
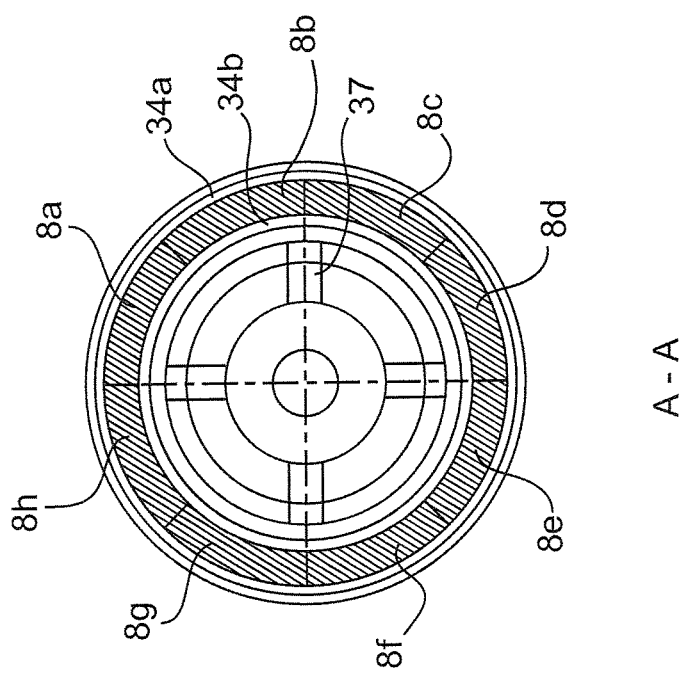
Figure 9:
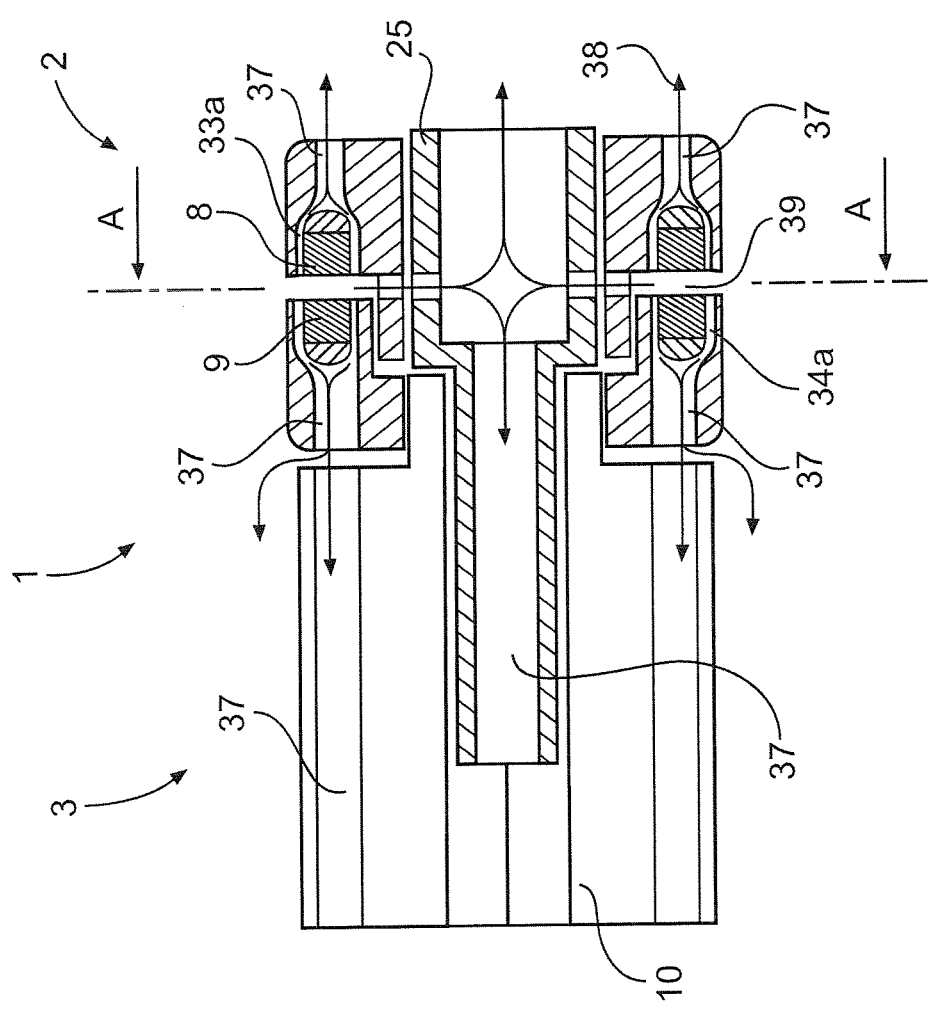
Figure 11:
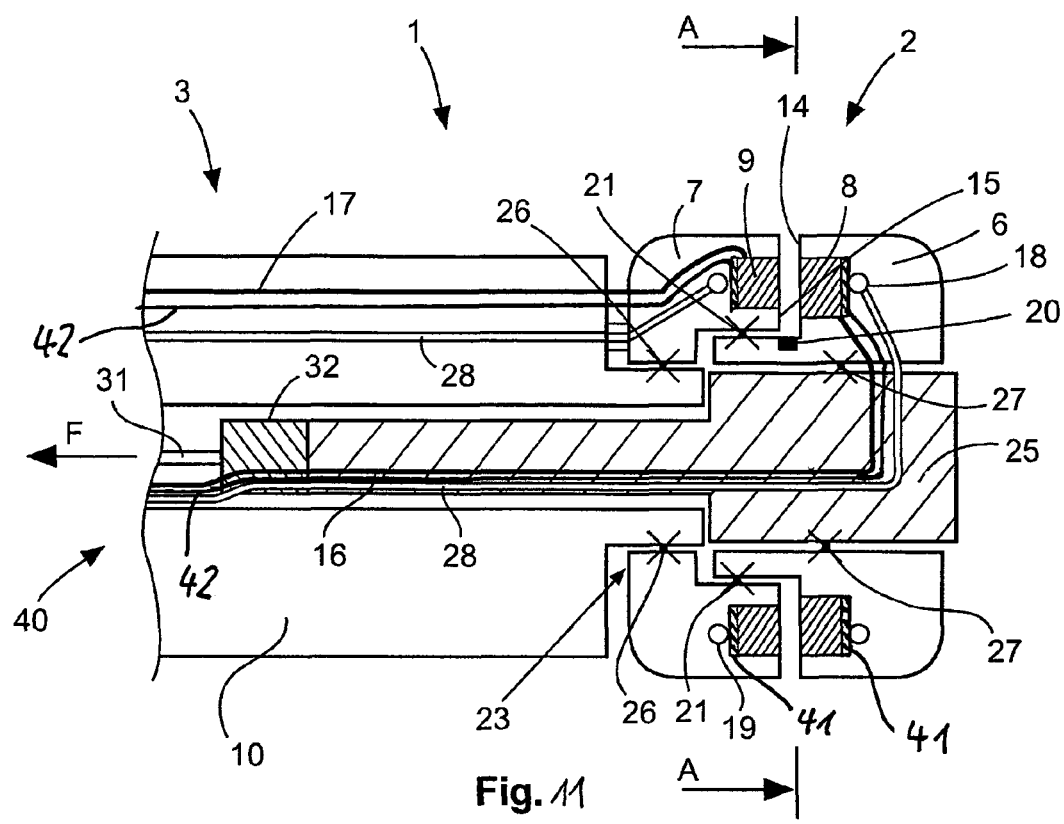

FIGS. 4a-c illustrate a schematic view of another embodiment of an anastomosis ring according to the invention;

FIGS. 5a-d illustrate a schematic view of an anastomosis of a hollow organ through an embodiment of the anastomosis ring according to the invention;

FIG. 6 illustrates a schematic view of a support ring according to the invention from FIG. 3 and a side view along a line A-A;

FIG. 7 illustrates a schematic sectional view of a distal end of another embodiment of the anastomosis ring assembly with the anastomosis ring according to the invention;

FIG. 8 illustrates a schematic view of a support ring according to the invention according to FIG. 7 in a lateral view along a line A-A;

FIG. 9 illustrates a schematic sectional view of the distal end of another embodiment of the anastomosis ring assembly according to the invention with anastomosis ring;

FIG. 10 illustrates a schematic view of the support ring according to the invention according to FIG. 9 in a lateral view along a line A-A;

FIG. 11 illustrates a schematic view of another embodiment of an anastomosis ring according to the invention.

Initially an anastomosis ring assembly according to the invention with an anastomosis ring will be described with reference to the exemplary embodiments in FIG. 1 and FIG. 3.

Figure 1:
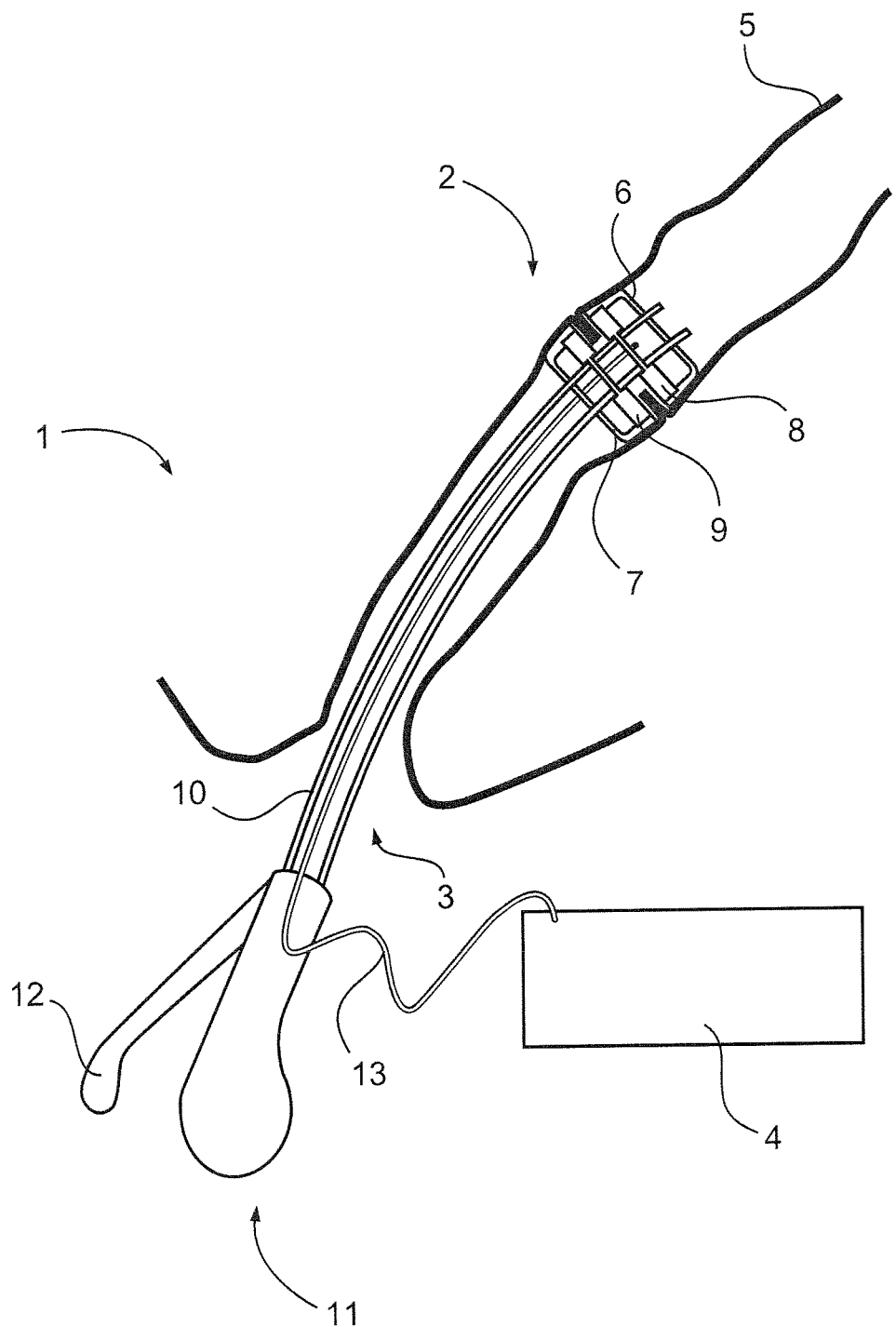
FIG. 1 illustrates a schematic sectional view of an anastomosis ring assembly according to the invention with an anastomosis ring for an intestinal anastomosis.

FIG. 1 illustrates and anastomosis ring assembly 1 with an anastomosis ring 2 and an applicator 3 during the anastomosis of intestinal tissue 5. The anastomosis ring assembly 1 is electrically connected with a HF generator 4.

The anastomosis ring 2 includes a first distal support ring 6 and a second proximal support ring 7. Each support ring 6, 7 respectively includes an electrode 8, 9 as an energy delivery element. The exact configuration of the anastomosis ring 2 is described infra in more detail with reference to FIG. 3.

The applicator 3 includes an elongated shaft 10 which is connected at its distal end with the anastomosis ring 2. At the proximal end of the shaft 10 a handle 11 and an actuation lever 12 are disposed at the applicator 3. An energy conductor 13 extends partially within the applicator 3 and electrically connects the electrodes 8, 9 with the HF generator 4. Thus, the energy conductor 13 includes at least two leads 16, 17 electrically shielded from one another, which connect bipolar electrodes 8, 9 with different poles (not shown) of the HF generator 4.

The HF (high frequency) generator 4 generates a high frequency AC voltage during its operation, wherein the voltage is configured for fusing tissue.

FIG. 3 illustrates the anastomosis ring 2 according to the invention and the distal end of the applicator 3 in a schematic sectional view which will now be described in more detail.

The anastomosis ring 2 includes a first distal support ring 6 and a second proximal support ring 7. The support rings 6, 7 are configured as rotation symmetrical rings in this embodiment, wherein the rings are disengageably connected with one another. The support rings 6, 7 respectively include a support surface 14, 15. In the illustration in FIG. 3 in which the support rings 6, 7 are connected with one another; the support surfaces 14, 15 are disposed opposite to one another and substantially parallel to one another.

Each support ring 6, 7 includes an electrode 8, 9, the distal support ring 6 includes a o distal electrode 8 and the proximal support ring 7 includes a proximal electrode 9. In the embodiment in FIG. 3 the electrodes 8, 9 are integrated into the support rings 6, 7 and form a portion of the support surfaces 14, 15. In order to prevent tissue from sticking, the support surfaces 14, 15 are fabricated essentially smooth without transition edges or protrusions to the electrodes 8, 9. The electrodes 8, 9 are disposed in the support rings 6, 7, so that they are disposed essentially opposite to one another when the support rings 6, 7 are inserted into one another. The electrodes 8, 9 are respectively electrically connected with different leads 16, 17 of the energy conductor 13.

In the embodiment in FIG. 3, the electrodes 8, 9 are configured as ring electrodes as illustrated in FIG. 6 in a lateral view along the line A-A in FIG. 3. Alternatively each electrode 8, 9 can include several particular electrodes connected in series which are disposed in the support surface 14, 15 of the support rings 6, 7 in a circular shape.

In the portion of the electrodes 8, 9 and of the support surfaces 14, 15 respective coolant channels 18, 19 are disposed in the support rings 6, 7, through which a coolant like e.g. saline solution can be run.

The distal support ring 6 includes a temperature sensor 20 in the portion of the support surface 14. Thus, the temperature sensor 20, different from the embodiment in FIG. 3, can also be disposed directly in the portion of an electrode 8, 9. The temperature sensor 20 is operatively connected with the HF generator 4 through a signal conductor, which is not shown.

In the embodiment in FIG. 3 the support rings 6, 7 are disengageably connected with one another through a connection element 20. Any suitable mechanical connection can be used as a connection element, like e.g. a snap lock connection, a threaded connection, a clamped connection or a wedged connection. Alternatively e.g. also a magnetic connection is feasible. It is crucial that the support rings 6, 7 can be secured and locked by the connection element 12 against pulling apart in axial direction.

The two annular support rings 6, 7 which can be connected with one another form an opening 22 of the anastomosis ring 2 in connected condition.

In the illustration in FIG. 3 the anastomosis ring 2 is placed onto the distal end of the applicator 3. For this purpose the shaft 10 of the applicator 3 is stepped at the distal end to form a support 23 on which the proximal support ring 7 is placed in the condition in FIG. 3. Thus, the support ring 7 is releasable coupled with the support 23 through a connection mechanism 26.

Furthermore, the applicator 3 includes a mandrel 25 on which the distal support ring 6 is placed in FIG. 3. The distal support ring 6 is disengagebly coupled with a mandrel 25 through a connection mechanism 27. The mandrel 25 extends within the shaft 10 and is moveable relative to the shaft 10 through an adjustment wheel 29 as illustrated in FIG. 4*a*. The adjustment wheel 29 is connected with the mandrel 25 in the interior of the applicator 3 though a transmission (not shown), a connection bar 31 and a disengageable clutch 32. Thus, the mandrel 25 is moveable relative to the shaft 10.

The connection mechanisms 26, 27 for connecting the anastomosis ring 2 with the applicator 3 can be implemented e.g. through two spreader mandrels which can be actuated independently from one another and which are actuated through another actuation lever or through a manual switch (not shown).

The leads 16, 17 of the energy conductor 13 and supply channels 28 extend in the shaft 10, in the mandrel 25 and in the coupling 32 in order to connect the electrodes 8, 9 to the HF generator 4 and the coolant channels 18, 19 to a coolant cycle (not shown). In order to transmit power or coolant, fluid connections and/or electrical connections can be disposed between the shaft 10 and/or the mandrel 25 and the anastomosis ring 2 in order to assure a good transition without losses.

Subsequently, the function of the anastomosis ring assembly 1 according to the invention with the anastomosis ring 2 is described with reference with FIG. 4.

FIG. 4*a* illustrates an embodiment of the anastomosis ring assembly 1 according to the invention in a state in which the anastomosis ring 2 is placed onto the applicator 3. The anastomosis ring assembly 1 is connected with the HF generator 4 through the energy conductor 13. The applicator 3 includes the adjustment wheel 29 at the proximal end of the handle 11. The axial distance B of the support rings 6, 7 relative to one another can be adjusted by turning the adjustment wheel 29.

The fusion of tissue is initiated in the embodiment in FIG. 4 through actuating the lever 12. Thus, the actuation lever 12 in the interior of the applicator 3 is connected with an electrical switch (not illustrated) which connects the bipolar electrodes 8, 9 with the output poles of the HF generator 4 in a first actuation position of the lever 12. Thus, HF current flows through tissue portions disposed between the electrodes 8, 9 and the tissue is thus fused. When pressing the lever 12 over into a second actuation position, which is disposed behind the first actuation position, the distance B between the support surfaces 14, 15 is reduced additionally in order to impart a fusion force F onto the tissue during tissue fusion.

The fusion force F is generated by a fusion force unit 40. The fusion force unit 40 illustrated in FIG. 3 and FIG. 4*a* in the embodiment includes a lever 12, a transmission (not illustrated) a connection rod 31, a clutch 32, a mandrel 25 and a distal support ring 6. Through the level 12 the fusion force F can be adjusted by the operator through the adjusted stroke.

At the handle 11 of the applicator 3 several hand switches 30 are disposed. When actuating a first hand switch 30*a* the clutch 32 in the interior of the applicator 3 is disengaged and the anastomosis ring 2 can be disassembled as illustrated in FIG. 4*b*. Thus, the distal support ring 6 and the mandrel 25 which are still connected with one another are separated from the rest of the anastomosis ring assembly 1. When actuating a second hand switch 30*b*, the connection mechanisms 26, 27 between the anastomosis ring 22 and the shaft 10 or the mandrel 25 are disengaged. As illustrated in FIG. 4*c*, the anastomosis ring 2 can be disengaged from the applicator 3.

Subsequently, the use of the anastomosis ring assembly 1 according to the invention with the anastomosis ring 2 is described with reference to the embodiment of an intestinal anastomosis according to FIG. 5.

Figure 5A:
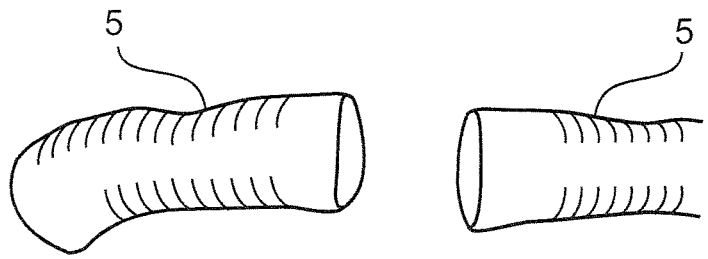
Figure 5B:
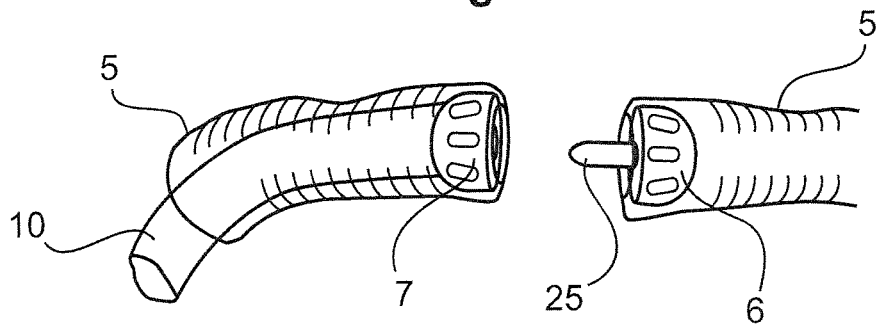
Figure 5C:
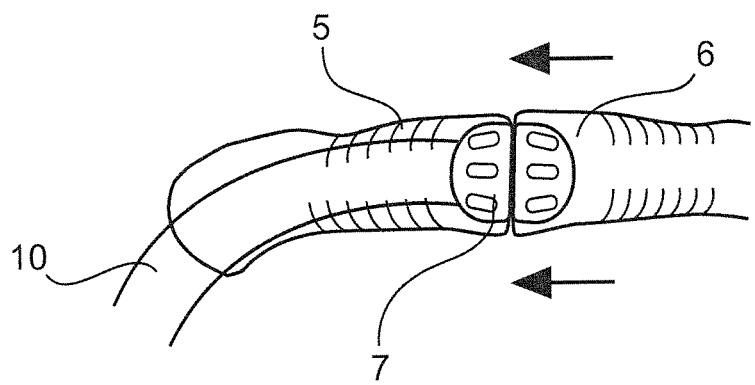
Figure 5D:
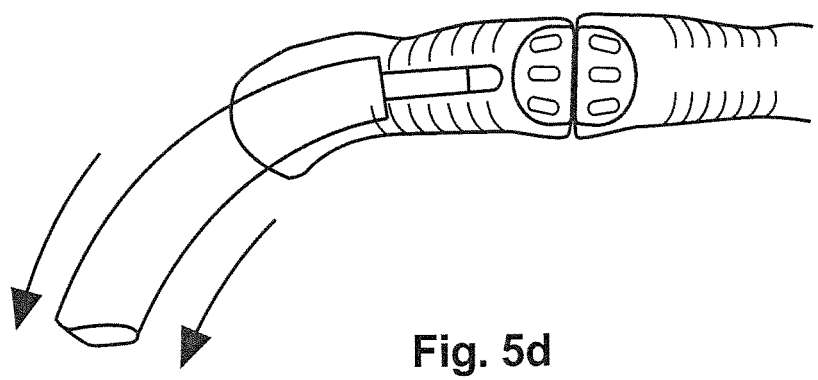

FIG. 5*a* illustrates two intestinal parts 5 before anastomosis. The anastomosis ring assembly 1 is initially disassembled into the two components state as illustrated in FIG. 4*b* for anastomosis. Then the distal support ring 6 placed onto the mandrel 25 is inserted into an intestinal component 5 and the remaining anastomosis ring assembly 1 with the proximal support ring 7 placed onto the shaft 10 is inserted into the other intestinal piece as illustrated in FIG. 5*b*. In the next step which is illustrated in FIG. 5*c*, the distal support ring 6 and the mandrel 25 are put together with the rest of the anastomosis ring assembly 1. Thus, the mandrel 25 is inserted into the shaft 10 and connected there with the coupling 32. The support rings 6, 7 are pulled together through rotating the adjustment wheel 29. Thus, the support rings 6, 7 engage one another and snap lock through the connection element 21, which can e.g. be configured as a snap lock element.

Subsequently, thermal tissue fusion is initiated through the actuation lever 12. Over the course of the tissue fusion a high frequency AC current flows from the one electrode 8, 9 through the tissue 5 retained in the anastomosis ring 2 to the other electrode 8, 9 and welds the tissue 5 together. A surgeon can decide at this point in time, if he wants to apply the fusion force F through pressing the actuation lever 12 over as described supra. Experiments have shown that this can be advantageous. In an advantageous embodiment of the invention the HF generator 4 stops the fusion process automatically based on predetermined tissue parameters. The tissue parameters can be e.g. the temperature determined by the temperature sensor 20, the tissue impedance or the Ohm tissue resistance or also the so called Eddy current effect.

Figure 2:
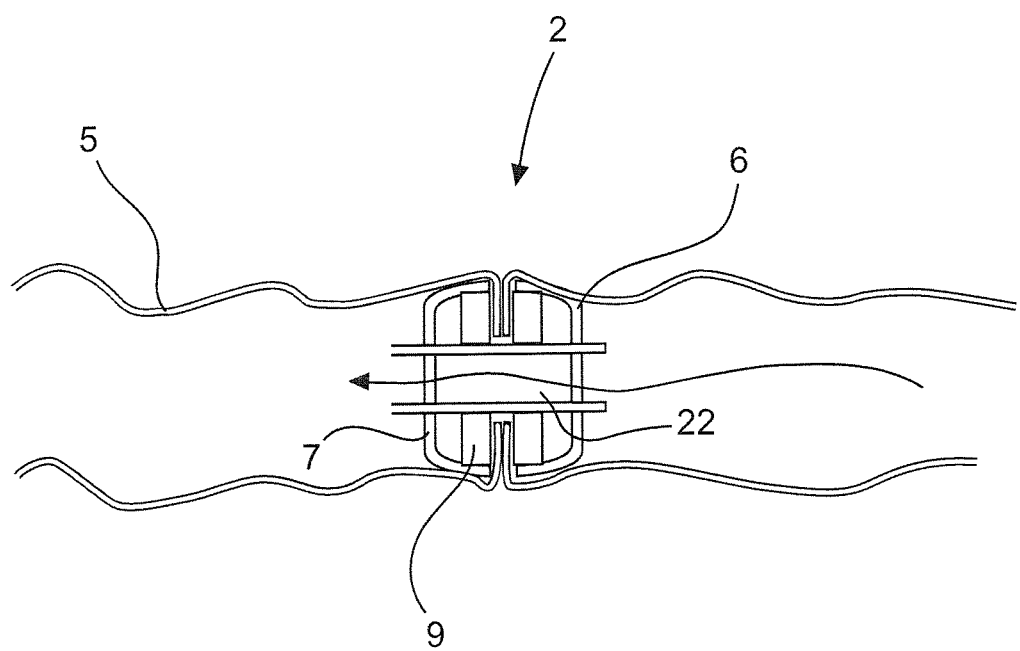
FIG. 2 illustrates a schematic view of an anastomosis ring according to the invention according to FIG. 1

After the tissue fusion is performed, the anastomosis ring 2 is decoupled from the applicator 3 as already described supra and as illustrated in FIG. 4*c*. Thus, also the connection of the electrodes 8, 9 to the HF generator 4 is separated. The applicator 3 is removed from the intestine and the anastomosis ring 2 remains in the body. The anastomosis ring 2 supports the fused intestinal tissue after the fusion until the natural wound healing has started additionally. While the anastomosis ring 2 remains in the body, the natural intestinal activity can continue since a movement of the intestinal content through the opening 22 of the anastomosis ring is possible as illustrated in FIG. 2.

After a predetermined time period which is sufficient for wound healing, the disintegration of the anastomosis ring 2 starts automatically. In the embodiment in FIG. 3 also the electrodes 8, 9 are made from bioresorable material. Portions of the anastomosis ring 2 which do not disintegrate are excreted from the intestine in a natural way. The electrodes 8, 9 can also be disengageably mounted in the anastomosis ring 2 and can be removed from the body e.g. through an applicator 3 after the fusion has been performed.

Subsequently another embodiment of the anastomosis ring 2 according to the invention is described with reference to FIGS. 7 and 8. The illustrated applicator 3 according to the invention is essentially identical with the embodiment in FIG. 3. Therefore, for reasons of brevity it not described again. With reference to the embodiment of the anastomosis ring 2 only the differences over the embodiment in FIG. 3 will be described.

The anastomosis ring 2 in FIG. 7 differs from the embodiment in FIG. 3 through the outlet channels 33a, 33b, 34a, 34b which are configured in the support surfaces 14, 15.

During thermal fusing of tissue a liquid and/or a gas is generated in the tissue. In order to improve the thermal dissipation in the tissue and to keep the water content of the tissue low, this fluid is run out in the anastomosis ring 2 according to the invention in FIG. 7 through the outlet channels 33a, 33b, 34a, 34b. The configuration of the outlet channels in a fusion instrument is known from the U.S. Patent application US2008/0195091A1.

In a proximal support ring 7 the outlet channels 34a, 34b are formed in the support surface 15 laterally from the electrode 9. In the distal support ring 8 the outlet channels 33a, 33b are formed in the support surface 14 laterally from the electrode 8 as illustrated in FIG. 8. In order to drain the fluid during tissue fusion from the outlet channels 33a, 33b, 34a, 34b, additional drainage openings 35, 36 are provided in the embodiments of FIGS. 7 and 8. The drainage openings 35 extend radially the drainage openings 36 extend axially.

The coolant channels 18, 19 are not illustrated in the illustrations in FIGS. 7-10 for reasons of improved clarity. However, they exist as well as all other details from the illustration in FIG. 3, which are not illustrated.

Subsequently another embodiment of the anastomosis ring 2 according to the invention is described with reference to FIGS. 9 and 10. The illustrated applicator 3 according to the invention is essentially identical with the embodiments in FIGS. 3 and 7. Therefore, for reasons of brevity it is not described again. With respect to the configuration of anastomosis ring 2 only differences over the embodiments in FIGS. 3 and 7 are described.

The anastomosis ring assembly in FIG. 9 differs from the embodiment in FIG. 7 through the pressure relief channels 37. The pressure relief channels 37 extend in the anastomosis ring 2 initially from a tissue fusion portion 39 between the electrodes 8, 9 in axial direction and in radially inward direction. The pressure relief channels 37 extending in axial direction connect to the drainage channels 33, 34. Pressure relief channels 37 also extend in the mandrel 25 of the applicator 3 in axial direction, wherein the pressure relief channels 37 are connected with pressure relief channels 37 radially extending in the tissue fusion portion 39 in the anastomosis ring 2. Pressure relief channels 37 are also configured in the shaft 10 of the applicator 3 for removing the water vapor 38, wherein the pressure relief channels 37 can be coupled with the axially extending pressure relief channels in the anastomosis ring 2. The pressure relief channel 37 terminate at the outside of the anastomosis ring 1, where a pressure relief to ambient pressure can take place.

During the tissue fusion with the anastomosis ring 2 according to the invention, the tissue fusion portion 39 is filled with tissue 5. In tests it has become apparent that a pressure increase and positive pressure can occur within the anastomosis ring 2 during the tissue fusion through the exiting water vapor. This pressure increase is prevented through the pressure relief channels 37. Without the pressure relief channel 37 the pressure can become high enough, so that the water vapor escapes through the fresh fusion seam for pressure relief, so that the tissue fusion gets damaged or destroyed. The pressure relief channels 37 drain the water vapor 38 in a controlled manner and thus provide the necessary pressure relief.

The electrodes 8, 9 are formed in the embodiment in FIGS. 9 and 10 differently from the prior embodiments as electrode assemblies made from single electrodes that are electrically connected. As evident from the illustration in FIG. 10, the particular electrodes 8a-8h form the annular electrode 8. The particular electrodes 8a-8h are made from a non bioresorable material like stainless steel. They are secreted from the intestine in a natural way after the rest of the bioresorable anastomosis ring 2 has disintegrated. The use of single electrodes 8a-8h has the advantage that they are flexible relative to one another after the rest of the remaining anastomosis ring 2 has disintegrated and can therefore be excreted more easily.

FIG. 11 illustrates another embodiment of the anastomosis ring 2 according to the invention. For reasons of simplicity only the differences over the embodiment in FIG. 3 are addressed.

The anastomosis ring 2 of FIG. 11 includes additional heating elements 41 in addition to the electrodes 8, 9. A heating element 41 is respectively associated with an electrode 29. The heating elements 41 are resistive heating elements, which are connectable with an energy source through the electrical conductors 42 in order to heat the tissue to be fused. Heating through the heating elements 41 is performed in addition to heating the tissue through the electrodes 8, 9.

The invention claimed is:

1. An anastomosis ring for connecting hollow organs made from human or animal tissue, comprising:
    a first support ring and a second support ring, which can be coupled with the first support ring for fixating the tissue, so that the support rings are essentially disposed fixated relative to one another,
    wherein the anastomosis ring further comprises at least one energy delivery element connectable with an energy source, wherein the energy delivery element is configured to fuse the tissue at least in sections through delivering energy during operations,
    wherein at least one drainage channel is configured in at least one of the support surfaces, and
    wherein fluid generated in the tissue during fusing can be drained through the drainage channel.

2. The anastomosis ring according to claim 1, wherein the anastomosis ring is at least partially made from a biofragmentable material which disintegrates after a predetermined time period in a human or animal body.

3. The anastomosis ring according to claim 1, wherein the first support ring comprises a first support surface and the second support ring comprises a second support surface, wherein the support surfaces support the tissue during fusing and the energy delivery element is disposed, so that it forms one of the support surfaces at least in sections.

4. The anastomosis ring according to claim 1, wherein the anastomosis ring comprises two energy delivery elements respectively associated with the two support rings and configured as HF electrodes, wherein the energy delivery elements are connectable with a HF energy source.

5. An anastomosis ring for connecting hollow organs made from human or animal tissue, comprising:
    a first support ring and a second support ring, which can be coupled with the first support ring for fixating the tissue, so that the support rings are essentially disposed fixated relative to one another, wherein the anastomosis ring further comprises at least one energy delivery element connectable with an energy source, wherein the energy delivery element is configured to fuse the tissue at least in sections through delivering energy during operations, wherein the anastomosis ring further comprises at least one pressure relief channel, through which a fluid pressure which differs from the ambient pressure and which is created during fusion in the anastomosis ring can be relieved.

6. The anastomosis ring according to claim 1, wherein the anastomosis ring comprises at least one temperature sensor through which the temperature of tissue can be detected.

7. An anastomosis ring for connecting hollow organs made from human or animal tissue, comprising:
   a first support ring and a second support ring, which can be coupled with the first support ring for fixating the tissue, so that the support rings are essentially disposed fixated relative to one another,
   wherein the anastomosis ring further comprises at least one energy delivery element connectable with an energy source, wherein the energy delivery element is configured to fuse the tissue at least in sections through delivering energy during operations,
   wherein the anastomosis ring further includes at least one coolant liquid channel extending at least in the portion of the energy delivery element, and
   wherein a liquid coolant can be passed through the coolant liquid channel.

8. The anastomosis ring according to claim 1, wherein the anastomosis ring includes at least one resistive electric heater element.

9. An anastomosis ring assembly for connecting hollow organs made from human or animal tissue with at least one anastomosis ring according to claim 1, comprising at least one applicator removably connected with the anastomosis ring for disposing the anastomosis ring within a body and comprising at least one energy conductor, whose first end is operatively connected with the energy delivery element and whose other end is connectable with the energy source.

10. The anastomosis ring assembly according to claim 9, wherein the energy conductor is connected to the applicator at least in sections and/or extends within the applicator.

11. The anastomosis ring assembly according to claim 9, wherein the anastomosis ring assembly includes a fusion force unit which applies a predetermined fusion force at least during fusing, wherein the fusion force presses the tissue portions against one another, which are to be fused.

12. An anastomosis ring assembly for connecting hollow organs made from human or animal tissue, comprising:
   an anastomosis ring comprising:
      a first support ring and a second support ring, which can be coupled with the first support ring for fixating the tissue, so that the support rings are essentially disposed fixated relative to one another; and
      at least one energy delivery element connectable with an energy source, wherein the energy delivery element is configured to fuse the tissue at least in sections through delivering energy during operations; and
   at least one applicator removably connected with the anastomosis ring for disposing the anastomosis ring within a body and comprising at least one energy conductor, whose first end is operatively connected with the energy delivery element and whose other end is connectable with the energy source; and
   a fusion force unit which applies a predetermined fusion force at least during fusing, wherein the fusion force presses the tissue portions against one another, which are to be fused,
   wherein the fusion force unit comprises an adjustment unit through which the fusion force is adjustable.

13. An anastomosis ring assembly for connecting hollow organs made from human or animal tissue, comprising:
   an anastomosis ring comprising:
      a first support ring and a second support ring, which can be coupled with the first support ring for fixating the tissue, so that the support rings are essentially disposed fixated relative to one another; and
      at least one energy delivery element connectable with an energy source, wherein the energy delivery element is configured to fuse the tissue at least in sections through delivering energy during operations; and
   at least one applicator removably connected with the anastomosis ring for disposing the anastomosis ring within a body and comprising at least one energy conductor, whose first end is operatively connected with the energy delivery element and whose other end is connectable with the energy source; and
   a fusion force unit which applies a predetermined fusion force at least during fusing, wherein the fusion force presses the tissue portions against one another, which are to be fused,
   wherein the fusion force unit is configured to apply at least two different fusion forces during fusing.

14. A kit for an anastomosis ring assembly for connecting hollow organs made from human or animal tissue, comprising at least one anastomosis ring according to claim 1 and at least one applicator for arranging the anastomosis ring within the body, wherein the applicator can be coupled with the anastomosis ring.

\* \* \* \* \*